(12) United States Patent
Haeg et al.

(10) Patent No.: US 6,205,358 B1
(45) Date of Patent: *Mar. 20, 2001

(54) METHOD OF MAKING ULTRASONICALLY WELDED, STAKED OF SWAGED COMPONENTS IN AN IMPLANTABLE MEDICAL DEVICE

(75) Inventors: Daniel C. Haeg, Champlin; Craig L. Wiklund, Bloomington; James F. Kelley, Coon Rapids, all of MN (US)

(73) Assignee: Medtronic, Inc., Minneapolis, MN (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/159,119

(22) Filed: Sep. 23, 1998

Related U.S. Application Data (62) Division of application No. 08/904,636, filed on Aug. 1, 1997, now abandoned.

(51) Int. Cl.[7] .................................................. A61N 1/362
(52) U.S. Cl. .............................................. 607/36; 29/857
(58) Field of Search .......................... 607/36–38; 29/825, 29/592.1, 854, 857

(56) References Cited

U.S. PATENT DOCUMENTS

| | | | |
|---|---|---|---|
| 3,842,842 | * 10/1974 | Kenny et al. ............................. | 607/36 |
| 4,041,956 | 8/1977 | Purdy et al. . | |
| 4,142,532 | 3/1979 | Ware . | |
| 4,182,345 | * 1/1980 | Grose ...................................... | 607/37 |
| 4,226,244 | * 10/1980 | Coury et al. ............................. | 607/37 |
| 4,445,511 | * 5/1984 | Cowdery et al. ........................ | 607/37 |
| 4,821,723 | 4/1989 | Baker, Jr. et al. . | |
| 5,131,388 | 7/1992 | Pless et al. . | |
| 5,144,949 | 9/1992 | Olson . | |
| 5,158,078 | 10/1992 | Bennett et al. . | |
| 5,199,428 | 4/1993 | Obel et al. . | |
| 5,207,218 | 5/1993 | Carpentier et al. . | |
| 5,282,841 | * 2/1994 | Szyszkowski .......................... | 607/36 |
| 5,312,453 | 5/1994 | Shelton et al. . | |
| 5,314,430 | 5/1994 | Bardy . | |

(List continued on next page.)

OTHER PUBLICATIONS

Branson Ultrasonics Corporation, "*Designing Parts for Ultrasonic Welding*", Technical Information, PW–3, 1975, revised Feb. 1996.
Branson Ultrasonics Corporation, "*TechnoLog—Today's Source for Plastics Joining Technology*", Apr. 1995.
Branson Ultrasonics Corporation, "*Ultrasonic Staking*" Technical Information, PW–6, revised Feb. 1996.

*Primary Examiner*—George R. Evanisko
(74) *Attorney, Agent, or Firm*—Thomas F. Woods; Harold R. Patton; Girma Wolde-Michael (57) ABSTRACT

The present invention generally relates to implantable medical devices and more particularly to various means for ultrasonically welding, swaging or staking various components in an implantable medical device, most preferably by employing appropriately configured covers or lids. Covers or lids are attached to header or connector modules mounted on an hermetically enclosed and sealed enclosure, where the connector or header module and enclosure comprise an implantable medical device. The covers or lids preferably trap or otherwise secure any of a number of various connector or header module components within the header or connector modules. Examples of such trapped or secured components include grommets, set screw connector blocks, seals, feedthrough wires, multi-beam contacts, electrical contacts, antennas, radio-opaque markers, connector ribbons and the like.

8 Claims, 7 Drawing Sheets

U.S. PATENT DOCUMENTS

| | | |
|---|---|---|
| 5,330,507 | 7/1994 | Schwartz . |
| 5,331,966 | 7/1994 | Bennett et al. . |
| 5,354,316 | 10/1994 | Keimel . |
| 5,456,698 | 10/1995 | Byland et al. . |
| 5,522,861 | 6/1996 | Sikorski et al. . |
| 5,535,097 | 7/1996 | Ruben et al. . |
| 5,545,186 | 8/1996 | Olson et al. ............ 607/14 |
| 5,558,641 * | 9/1996 | Glantz et al. ........... 604/93 |

* cited by examiner

METHOD OF MAKING ULTRASONICALLY WELDED, STAKED OF SWAGED COMPONENTS IN AN IMPLANTABLE MEDICAL DEVICE

CROSS-REFERENCE TO RELATED APPLICATIONS

This application is a division of application Ser. No. 08/904,636 filed Aug. 1, 1997 entitled "Ultrasonically Welded, Staked or Swaged Components in an Implantable Medical Device," to Haeg et al. now abandoned.

Reference is hereby made to commonly assigned, co-pending U.S. patent application Ser. No. 08/905,093 filed Aug. 1, 1997 for "Attachment Apparatus and Method for an Implantable Medical Device" to Rieder et al., U.S. patent application Ser. No. 08/904,601 filed Aug. 1, 1997 for "Attachment Apparatus and Method for an Implantable Medical Device Employing Ultrasonic Energy" to Wiklund et al., now U.S. Pat. No. 5,371,514 and U.S. patent application Ser. No. 08/877,033 filed Jun. 16, 1997 for "Attachment Apparatus and Method for an Implantable Medical Device Employing Ultrasonic Energy" to Rowley et al., the disclosures of which are hereby incorporated by reference herein in their respective entireties.

FIELD OF THE INVENTION

The present invention generally relates to implantable medical devices and more particularly to various means for ultrasonically welding, swaging or staking components of implantable medical devices in assemblies such as header modules through the use of appropriately configured covers or lids.

BACKGROUND OF THE INVENTION

The earliest implantable medical devices, e.g., implantable cardiac pacemakers and other body tissue stimulating devices, were formed of an implantable pulse generator (IPG) and a set of electrical leads attached between the IPG and heart or body tissue to be paced or stimulated. Typically, the IPG electrical circuit was powered either by Hg-Zn batteries or by induction of energy transmitted transcutaneously from a skin surface RF power generator and supplied electrical pacing or stimulating pulses to the leads. The IPG batteries and circuits were encapsulated within an epoxy compound partly for ease of manufacture and to allow hydrogen emitted by the Hg-Zn batteries to escape. Electrical connector pins and rings, if present, were initially permanently attached to the circuits. Other early implantable medical devices, e.g. implantable monitors and cochlear implants or the like were also formed in somewhat the same manner.

Such early implantable cardiac pacemakers suffered very short useful lives due to moisture ingress through the epoxy and causing electrical dendritic growth across, and shorting of, adjacent points of the circuit, battery terminals, or discrete transistor terminals. In addition, pacing leads frequently failed due to conductor stress fractures, and batteries depleted prematurely for a variety of reasons.

In the 1960's, IPG connector assemblies were formed integrally with other IPG circuit components and embedded in an epoxy housing to enable attachment of a chosen lead to the IPG circuit for initial implant or defective lead replacement purposes. These integrally formed connector assemblies typically comprised at least one metal, electrical connector block encapsulated therein that were aligned in relation to an elongated lead end receptacle for receiving the proximal lead end. Each connector block was formed to have a bore to receive the lead connector pin or ring, depending on the type of lead intended to be used, and a threaded cross bore receiving a trapped set screw. The electrical connections in connector blocks were typically directly attached to IPG circuits. A silicone rubber suture boot was placed in a mold in alignment with an elongated receptacle. The entire IPG, including connector assembly components, was then encapsulated in epoxy.

In use, a proximal lead connector end was inserted into the appropriate lead connector receptacle until the lead connector pin or ring was received in the bore of the connector block. A set screw was then tightened by a hex wrench to establish firm electrical and mechanical connections and the opening through the molded epoxy housing to access the set screw was sealed. Sutures were tied around the suture boot for sealing engagement against the lead body.

Beginning in the 1970s, hermetically sealed lithium batteries and miniaturized digital and analog integrated circuits (ICs) have been used in implantable medical devices, particularly for implantable cardiac pacemaker and nerve stimulation IPGs. Integrated circuits, batteries and other components were enclosed in hermetically sealed metallic enclosures or "cans" separated from the connector assembly components. Electrical connection between connector blocks and other components of the connector assembly was generally accomplished by electrical feedthroughs supporting feedthrough pins extending through the hermetically sealed can.

Lead connector assembly components external to the hermetically sealed enclosure are still to this date attached to an attachment surface thereof using an in situ molding process to seal the connector assembly components and form the receptacle for a lead or catheter proximal end, etc. For example, in the formation of a lead connector assembly for a cardiac pacemaker IPG, the connector blocks and feedthrough pins are welded together and laid out in a mold with respect to any other associated components and mold plugs. An encapsulating compound is injected into the mold to form the connector header assembly molded to the IPG attachment surface as described, for example, in U.S. Pat. No. 4,041,956, the disclosure of which is hereby incorporated by reference herein in its entirety. This approach is time consuming and not terribly precise. If the resulting connector header assembly fails to meet dimensional tolerances or other quality requirements, it is difficult to rework the IPG.

In 1979 the MEDTRONIC® SPECTRAX® cardiac pacemaker IPGs were introduced having the digital and analog or hybrid ICs and lithium batteries enclosed within a hermetically sealed titanium enclosure having feedthroughs extending through an enclosure attachment surface thereof. Assembly of these components and other details are disclosed in U.S. Pat. Nos. 4,142,532 and 4,182,345, hereby incorporated by reference herein in their respective entireties.

The lead connector assembly, in this case and as used in IPG models to the present time by Medtronic, Inc., is manufactured as a separate pre-formed connector header module that encloses connector components and is attached to an enclosure attachment surface of the hermetically sealed enclosure and to the feedthrough pins. The connector header module is molded of a thermoplastic elastomer such as medical grade polyurethane, has an outer module surface and a number of receptacles and channels disposed within it that in some instances are accessible through windows, channels or recesses extending outwardly to the module surface. The connector header module receives the electrical connector blocks)in connector block receptacles such that the connector block bores are aligned with elongated lead connector receptacles for receiving the proximal lead connector end assemblies. In a typical design, each such connector block is formed with a threaded cross bore receiving a trapped set screw as described above. Each set screw of each connector block in a connector block receptacle is also aligned with a septum receptacle for receiving a silicone rubber set screw septum.

A pre-formed connector header module is generally formed with pin channels for directing the feedthrough pins into contact with the respective connector blocks and with windows to allow the connector blocks and septums to be inserted into their respective receptacles. In each case, the connector block receptacle window or a further window to the module surface is provided for allowing the feedthrough pin end to be welded to the connector block. The windows and pin channels are typically back filled with a medical grade silicone adhesive after the welding step and attachment of the connector header module to the hermetically sealed enclosure.

The receptacle for the connector block and the connector block itself most preferably have fight dimensional tolerances to permit precise alignment of the connector block bore with the lead connector receptacle. In one approach, the connector block receptacle opening dimensions are reduced and the opening edge thereof shaped so that the connector block stretches the opening edge as it is inserted into the connector block receptacle. In other cardiac pacemaker IPGs, each connector block is inserted into a connector block receptacle and ultrasonic energy is applied to the edge of the connector block window to melt it over and tamp it against the exposed surface of the connector block. This ultrasonic tamping technique of dissimilar material parts is similar to that shown in the article entitled "Ultrasonic Joining of Moulded Parts and Semi-Finished Parts of Thermo-Plastic Polymers in Mass Production-Forming with Ultrasound," Staking, Swaging and Tamping (Guideline DVS 2216, Part 3, 1992), *Welding in the World, Le Soudage Dans Le Monde*, Vol. 31, No. 3, pp. 205–207 (1993), the disclosure of which is hereby incorporated by reference herein in its entirety.

As a general rule, a connector header module formed as described above must have tight dimensional tolerances and remain dimensionally stable over long periods of time in the hostile environment found within the human body. Any substantial initial or time-induced misalignment of the lead connector receptacle bores extending through the molded module housing and the connector block bores can make initial attachment or removal and replacement of a lead connector end impossible or unreliable. During the attachment of the connector header module to the hermetically sealed enclosure, medical grade adhesive is usually employed to attach the module attachment surface to the enclosure attachment surface. While the adhesive cures, it is necessary to ensure that the attachment surfaces are not disturbed.

Some workers in the field have proposed employing mechanical attachment mechanisms as a substitute for, or in addition to, the use of the medical grade adhesive for attaching surfaces to one another. Mechanical attachment mechanisms proposed in the art for use with or without medical grade adhesive are described in U.S. Pat. Nos. 4,142,532 and 4,182,345, both incorporated herein by reference in their respective entireties. While the approaches described in those patents have merit, they require the use of additional precision piece parts and assembly steps that may add to the cost and time required to assemble the connector header module and connect it to the hermetically sealed enclosure.

Finally, it should be noted that it has been recently proposed to form the connector header module as part of a shroud surrounding and adhering to the rim of the hermetically sealed enclosure in order to simplify the assembly by reducing the number of parts, assembly steps and dimensional tolerance requirements. Such configurations are shown in U.S. Pat. Nos. 5,535,097, 5,522,861, 5,456,698 and 5,431,695, all incorporated herein by reference in their respective entireties. In such configurations, the shroud is preferably formed of a flexible silicon rubber and pacing leads may be attached and replaced in conventional fashion. The use of silicone rubber presents certain difficulties and disadvantages, however, most of which relate to dimensional instability and lack of rigidity, lack of an aesthetically pleasing physical appearance and potential discoloration of the silicone rubber during storage and sterilization.

SUMMARY OF THE INVENTION

The present invention has certain objects. That is, the present invention provides solutions to at least some of the problems existing in the prior art such as:

(a) highly precise dimensional tolerances being required for injection mold tools employed to form connector or header module components, or connector or header modules;

(b) excessive flash occurring in connector or header module components, or connector or header modules, formed by injection molding means;

(c) hand trimming of flash being required in connector or header module components, or connector or header modules, formed by injection molding means;

(d) backfilling of voids, channels and the like with medical grade adhesive being required in connector or header module components, or connector or header modules;

(e) molded parts or components having flash disposed thereon having decreased biocompatibility;

(f) medical adhesive requiring long cure times;

(g) hand assembly or reworking steps being required to complete assembly of header or connector modules;

(h) parts or components requiring preparation to permit or enhance adhesion of medical adhesive to desired surfaces;

(I) post-assembly steps being required for cleaning up and removing medical adhesive; and (j) medical adhesive having insufficient structural or mechanical integrity to provide mechanical protection of electrical and mechanical parts disposed with a header or connector module.

Various embodiments of the present invention have certain advantages, including, but not limited to, at least some of the following:

(a) providing reduced structural complexity and dimensional tolerance requirements for injection molding tools employed to form header or connector modules or components therefor;

(b) eliminating or reducing substantially the use of medical adhesives to form connector or header modules;

(c) eliminating or reducing substantially the requirement for long cure times of medical adhesive;

(d) providing improved mechanical protection for parts or components disposed within the header or connector module;

(e) permitting the design and use of less expensive, less structurally complex, lighter, smaller and fewer parts or components for placement in a header or connector module;

(f) permitting the use of parts or components in header or connector modules that have improved performance characteristics respecting similar prior art parts or components;

(g) reducing manufacturing time;

(h) reducing manufacturing cost;

(I) providing increased manufacturing flexibility;

(j) providing increased part or component interchangeability between different models of implantable medical devices; and (k) reducing inventory costs.

Various embodiments of the present invention posses one or more of the following features:

(a) a cover or lid which matingly engages a corresponding recess disposed in the outer surface of a connector module or header, the lid or cover being ultrasonically welded thereto; and (b) a component or part disposed between or in a recess of a connector module or recess, a lid or cover matingly engaging or fitting over the recess, the lid or cover being ultrasonically welded to the connector or header module.

The foregoing and other objects, advantages and features of the present invention will be appreciated better by referring to the appended claims, drawings and detailed description.

BRIEF DESCRIPTION OF THE DRAWINGS

In the drawings, like reference numbers refer to like parts.

FIG. 4(*a*) is an exploded perspective view of one embodiment of a connector module of the present invention;

FIG. 4(*b*) is a top plan view of the connector module of FIG. 4(*a*);

FIG. 4(*c*) is a cross-sectional view of the connector module of FIG. 4(*a*);

DETAILED DESCRIPTION OF THE PREFERRED EMBODIMENTS

The preferred embodiments of the present invention relate to ultrasonic means for attaching or securing various components inside a pre-formed header module to thereby form an hermetically sealed enclosure. Implantable medical devices where the present invention finds application include implantable drug dispensers, IPGs (including cardiac pacemakers, pacemaker-cardioverter-defibrillators, nerve, muscle and neurological stimulators, cardiomyostimulators, etc.), implantable cardiac signal monitors and recorders and the like. Virtually all MEDTRONIC® electronic implantable medical devices that require attachment of a hermetically sealed power supply and circuitry to an interchangeable catheter or electrical lead employ a general configuration of a hermetically sealed enclosure in conjunction with a pre-formed header module.

Figure 1:
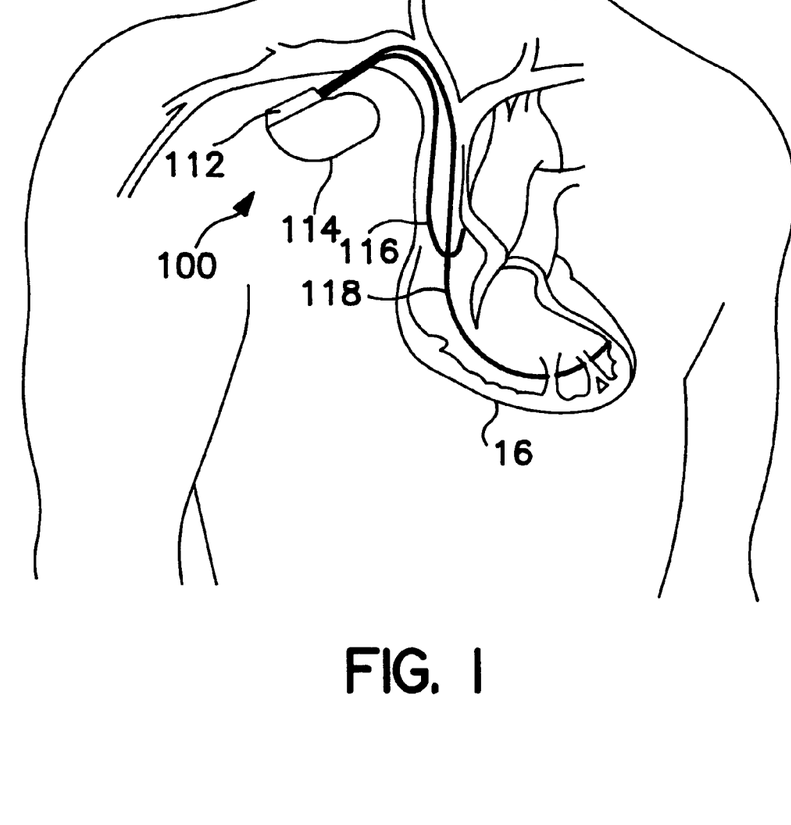
FIG. 1 shows a simplified schematic view of an implantable medical device of the present invention disposed in a human subject.

FIG. 1 is a simplified schematic view of an implantable medical device 100 embodying the present invention, where an improved pre-formed header module 112 is attached to an hermetically sealed enclosure 114 and implanted near human heart 16. In the case where implanted medical device 100 is a pacemaker it includes at least pre-formed header module 112 and one or both of pacing and sensing leads 116 and 118. Pacing and sensing leads 116 and 118 sense electrical signals attendant to the depolarization and re-polarization of the heart 16, and provide pacing pulses for causing depolarization of cardiac tissue in the vicinity of the distal ends thereof. Implantable medical device 100 may be an implantable cardiac pacemaker such as those disclosed in U.S. Pat. No. 5,158,078 to Bennett et al, U.S. Pat. No. 5,312,453 to Shelton et al, or U.S. Pat. No. 5,144,949 to Olson, all hereby incorporated herein by reference in their respective entireties.

Implantable medical device 100 may also be a PCD (Pacemaker-Cardioverter-Defibrillator) corresponding to any of the various commercially available implantable PCDs, with the substitution of connector module 112 of the present invention for the connector block assembly otherwise present. The present invention may be practiced in conjunction with PCDs such as those disclosed in U.S. Pat. No. 5,545,186 to Olson et al., U.S. Pat. No. 5,354,316 to Keimel, U.S. Pat. No. 5,314,430 to Bardy, U.S. Pat. No. 5,131,388 to Pless or U.S. Pat. No. 4,821,723 to Baker et al., all hereby incorporated herein by reference in their respective entireties. Those devices may be employed directly in conjunction with the present invention, and most preferably are practiced such that the feedthroughs interconnecting the circuitry therein to their connector blocks is located to permit ready access between the feedthroughs and the electrical connectors disposed within the connector bores of connector or header module 112.

Alternatively, implantable medical device 100 may be an implantable nerve stimulator or muscle stimulator such as that disclosed in U.S. Pat. No. 5,199,428 to Obel et al., U.S. Pat. No. 5,207,218 to Carpentier et al. or U.S. Pat. No. 5,330,507 to Schwartz, or an implantable monitoring device such as that disclosed in U.S. Pat. No. 5,331,966 issued to Bennet et al., all of which are hereby incorporated by reference herein in their respective entireties. The present invention is believed to find wide application to any form of implantable electrical device for use in conjunction with electrical leads, and is believed to be particularly advantageous in those contexts where multiple medical electrical leads are employed and desired.

In general, hermetically sealed enclosure 114 includes an electrochemical cell such as a lithium battery, circuitry that controls device operations and records arrhythmic EGM episodes, and a telemetry transceiver antenna and circuit that receives downlink telemetry commands from and transmits stored data in a telemetry uplink to the external programmer. The circuitry and memory may be implemented in discrete logic or a micro-computer based system with A/D conversion of sampled EGM amplitude values. The particular electronic features and operations of the implantable medical device are not believed to be of overriding significance in respect of practicing the present invention. One exemplary operating system is described in commonly assigned, co-pending U.S. patent application Ser. No. 08/678,219, filed Jul. 11, 1996, for "Minimally Invasive Implantable Device for Monitoring Physiologic Events," the disclosure of which is hereby incorporated by reference herein in its entirety.

Figure 2:
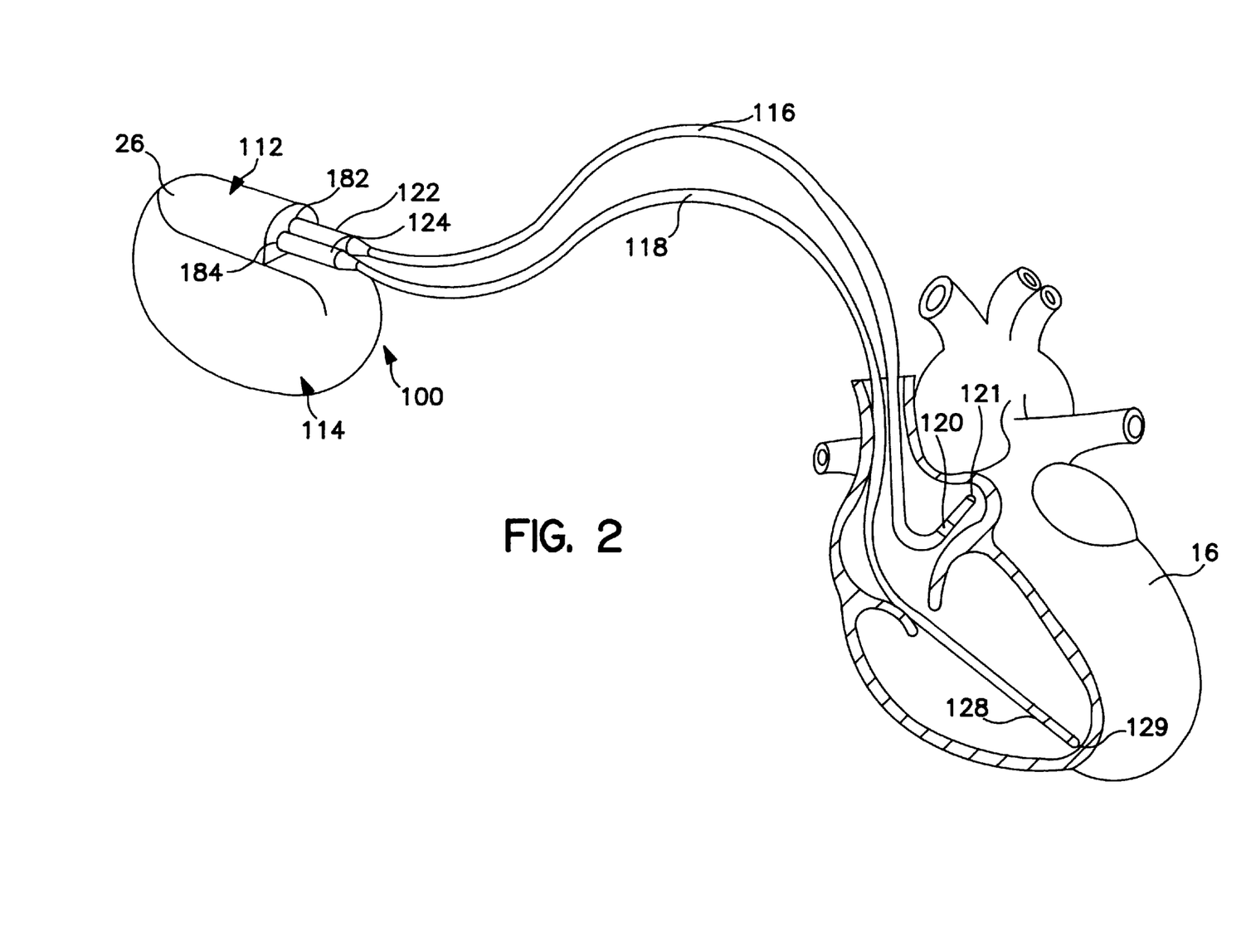
FIG. 2 shows an isometric view of a cardiac pacemaker and corresponding lead system of the present invention as they relate to a human heart; an exploded plan view of the header module in relation to the hermetically sealed enclosure of the implantable cardiac monitor of FIG. 1.

FIG. 2 depicts connector module 112 and hermetically sealed enclosure 114 of implantable medical device or dual chamber pacemaker IPG 100 of the present invention as they relate to patient's heart 16. Atrial and ventricular pacing leads 116 and 118 extend from connector header module 112 to the right atrium and ventricle, respectively. Atrial electrodes 120 and 121 disposed at the distal end of the atrial pacing lead 116 are located in the right atrium. Ventricular electrodes 128 and 129 at the distal end of ventricular pacing lead 118 are located in the right ventricle.

Connector header module 112 may take any of the forms described herein for establishing electrical and mechanical connections of proximal connector end assemblies 122 and 124 of the atrial and ventricular pacing leads 116 and 118 to electrical or electronic circuitry disposed within hermetically sealed enclosure 114. Connector header module 112 therefore preferably incorporates four connector blocks (not shown) within the module housing that are aligned with elongated lead connector end receptacles 182 and 184, and that are adapted to receive lead connector end assemblies 122 and 124. Header module 122 may be molded of a rigid thermoplastic material such polyurethane, polysulfone or any other such suitable medical grade thermoplastic material. Header module 122 has an exposed exterior surface and a number of receptacles and channels formed therein. Feedthroughs and feedthrough pins connected to the connector blocks and extending through the hermetically sealed enclosure 114 are also not shown in FIG. 2.

Figure 3:
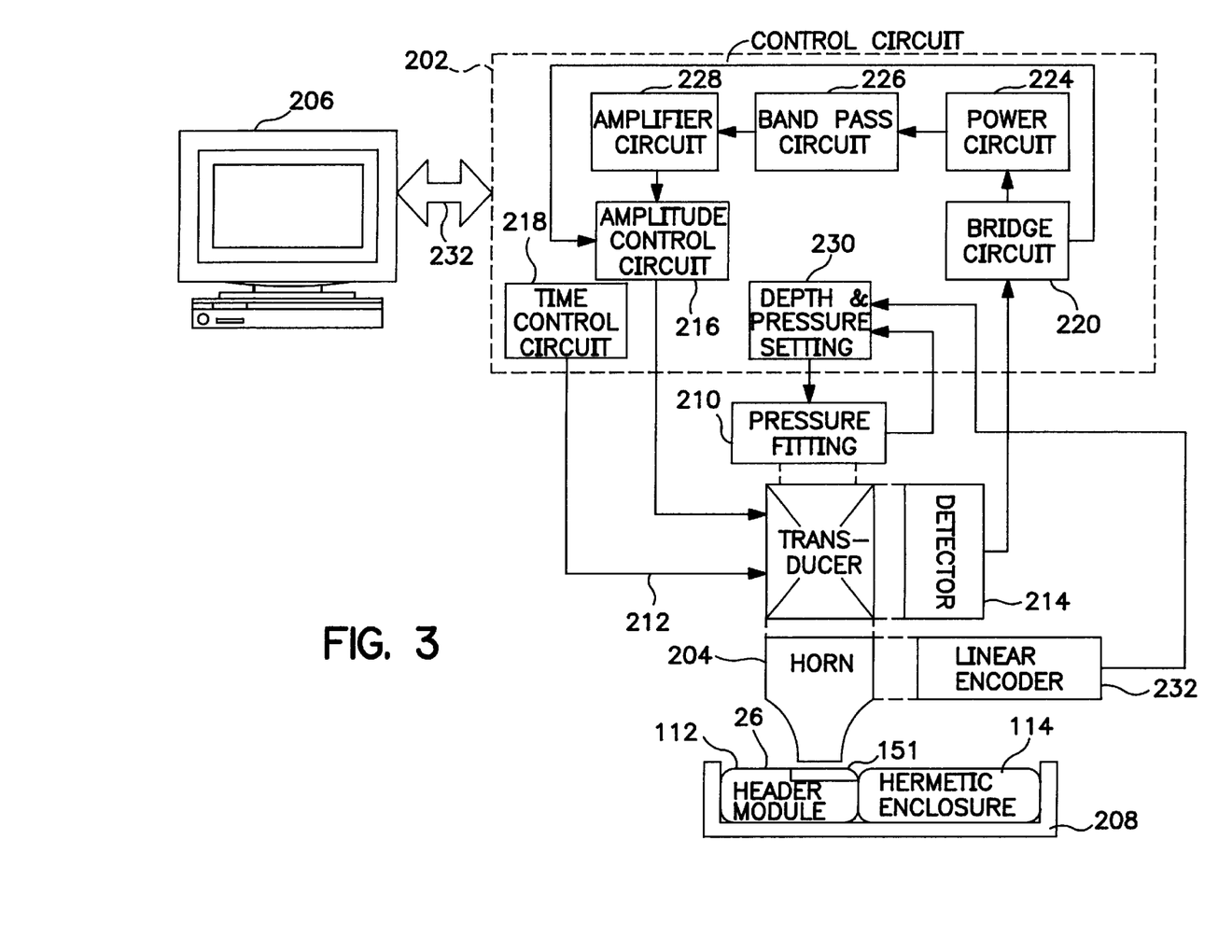
FIG. 3 shows a simplified block system diagram for employing ultrasonic welding energy in the attachment of various components, covers, lids and the like to a header module to form an hermetically sealed enclosure suitable for implantation within the human body.

FIG. 3 depicts an ultrasonic welding system and some of the manufacturing steps for ultrasonically attaching various components such as lids or covers to preformed header module 112. The system and corresponding methods of FIG. 3 are similar to those described in the article "Ultrasonic Pressing of Plastic-Film Capacitor" by S. Kaneko et al., at pp. 699–702 in *Ultrasonics International* 93 *Conference Proceedings*, (1993), and is representative of a computerized ultrasonic welding system sold by Branson Sonic Power Co. of Danbury, Conn. The attachment steps depicted in FIG. 3 most preferably follow the assembly and welding of the pre-formed header module to hermetically sealed enclosure 114 using upstanding tabs 152, 152', 154 and 154' and corresponding recesses as disclosed in U.S. patent application Ser. No. 08/904,601 for "Attachment Apparatus and Method for an Implantable Medical Device Employing Ultrasonic Energy" to Wiklund et al. filed Aug. 1, 1997 now U.S. Pat. No. 5,871,514.

Figures 4A, 4B:
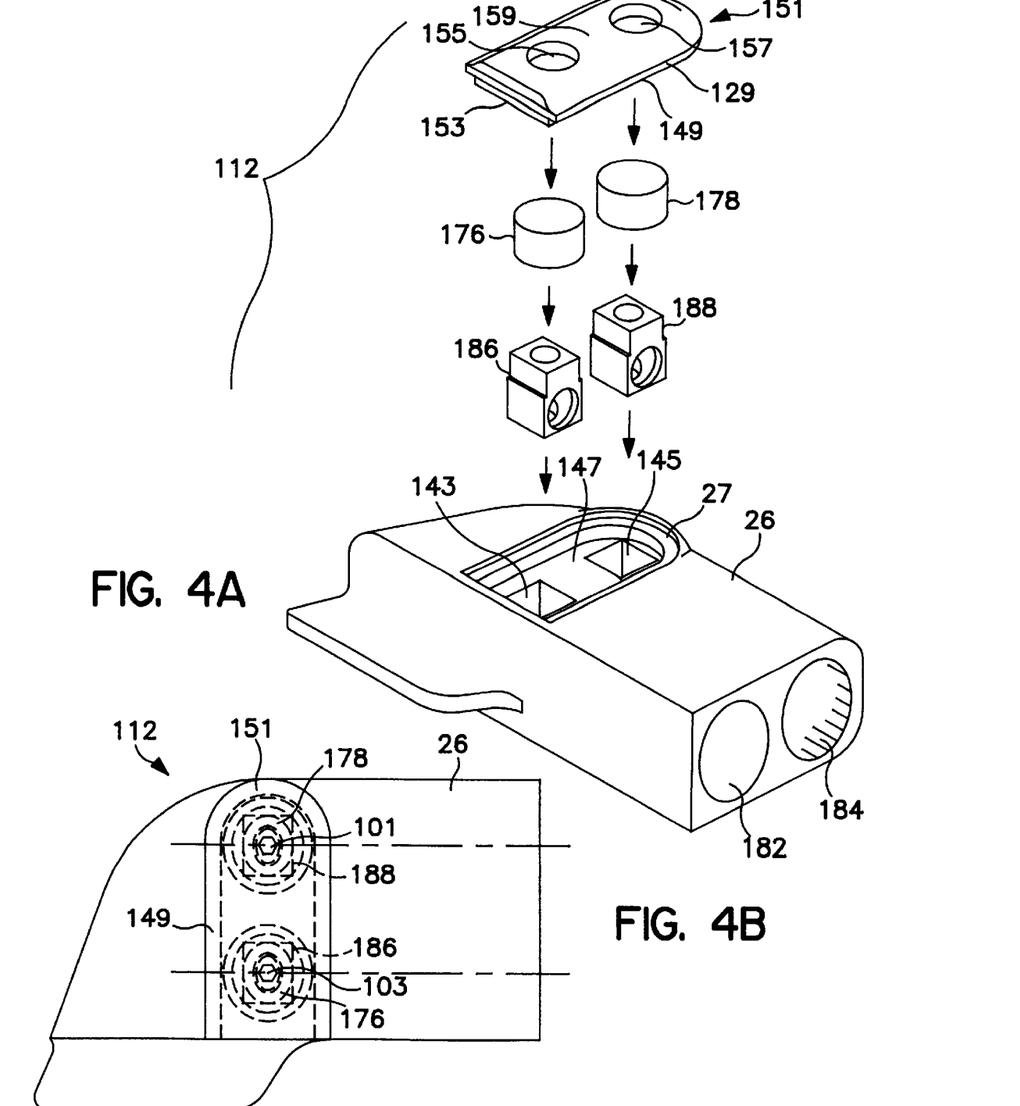
Figure 4C:
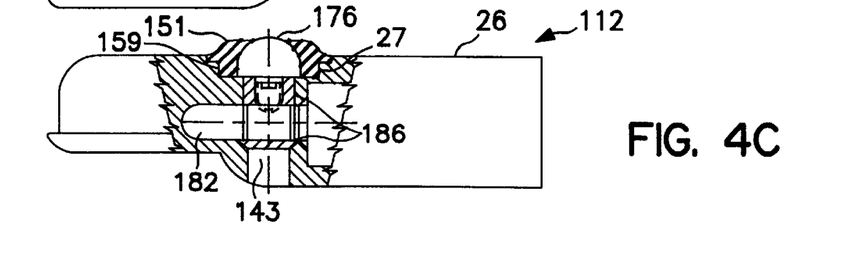
Figure 5:
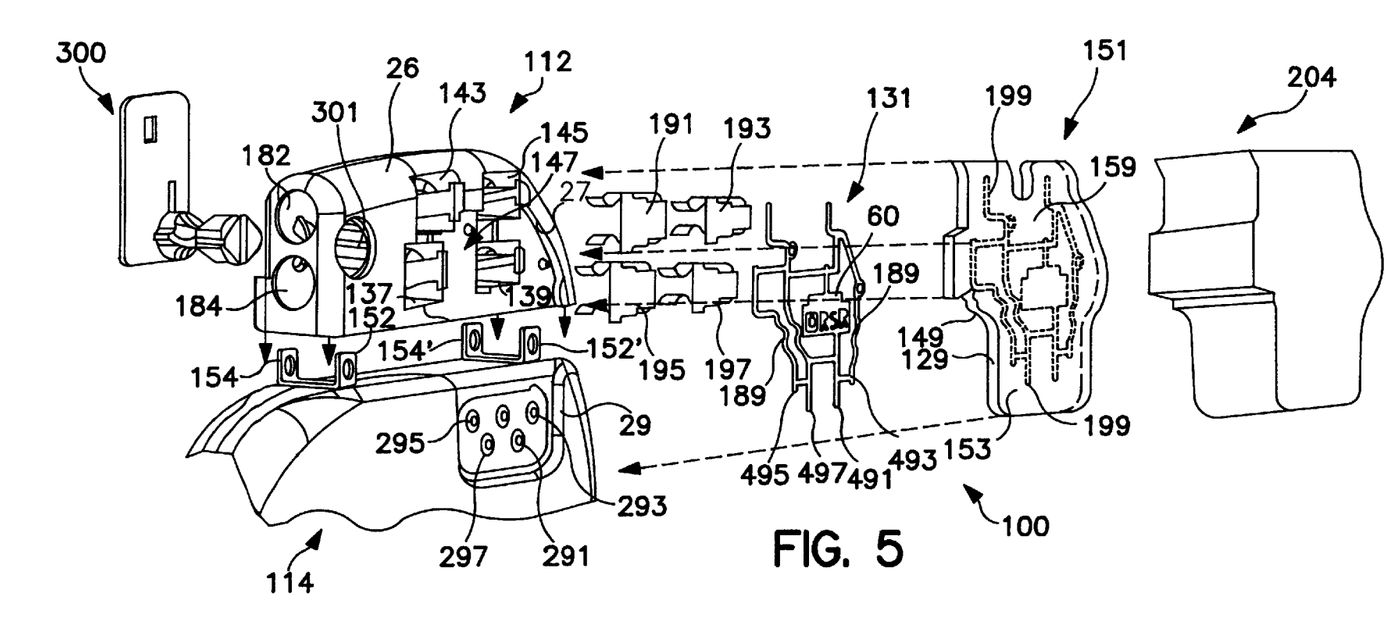
FIG. 5 is an exploded perspective view of another embodiment of a connector module and corresponding hermetically sealed IPG of the present invention.
Figure 6:
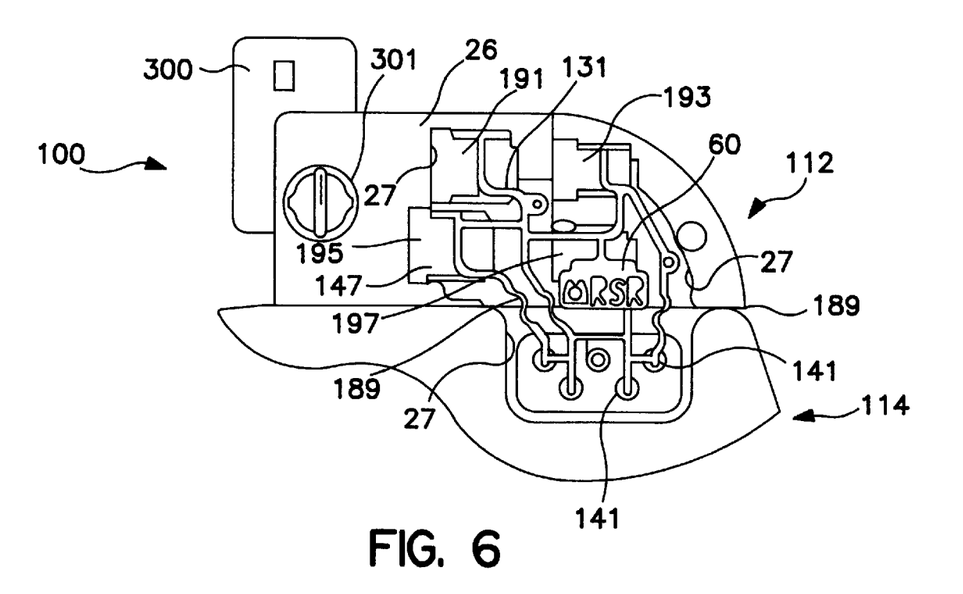
FIG. 6 is a side view of the connector module and corresponding hermetically sealed IPG of FIG. 5.

The attachment steps illustrated in FIG. 3 preferably follow attachment of the terminals of feedthrough pins 291, 293, 295 and 297 to MBCs (multiple beam contacts) 191, 193, 195 and 197 via ribbon connector 131 and subsequent removal of undesired metallization disposed between feedthrough contacts or wires 491, 493, 495 and 497 pins, as illustrated in FIGS. 5 and 6. Alternatively, the illustrated attachment steps may follow the emplacement of grommets 176 and 178 or setscrew blocks 186 and 188 within connector module 112 as illustrated in FIGS. 4(a) through 4(c).

Ultrasonic welding system 200 includes control circuit 202 for operating ultrasonic horn 204 to apply ultrasonic welding energy to the desired portions of header module 112 under the control of microprocessor based work station 206 that is controlled by a human operator. A human operator enters into work station 206 a desired applied static force value, a desired linear travel distance, a desired ultrasonic weld time and a desired cooling time following the ultrasonic weld time. The operator may select the amplitude of the ultrasonic vibrations of ultrasonic horn 204 and the ultrasonic frequency, although these may be fixed for each weld cycle in a given configuration of ultrasonic horn 204 and header module 112.

The vibration amplitude and frequency, the applied static force, and the period of time that horn 204 applies ultrasonic energy to a desired surface or portion of header module 112 may be selected by the operator. Those factors determine the amount of ultrasonic energy delivered to connector module 112. When ultrasonic energy is delivered to the module, ultrasonic energy is converted into heat energy to melt the thermoplastic material in a desired region. In preferred embodiments of the present invention, ultrasonic energy is employed to melt a mass of thermoplastic material extending from the horn surface laterally into a pre-formed channel or groove. The volume and depth of the melted mass is controlled by the shape and surface area of the horn surface of ultrasonic horn 204 and the depth to which horn 204 penetrates beneath the exterior surface of header module 112.

As the horn surface penetrates into the surface, it moves closer to any pre-formed channels that may be disposed within header module 112 as the thermoplastic material melts. The area of the melt then advances into the channel to form a mass of melted thermoplastic material therein. It is desirable to control the depth of penetration to ensure that the horn surface does not transmit ultrasonic energy directly into to hermetically sealed enclosure 114. The linear travel of horn 204 is preferably set to the dimensions of a selected particular header module 112 so that applied ultrasonic energy is concentrated in a region surrounding the channels to melt the adjoining thermoplastic material therein.

Entered ultrasonic weld cycle values are translated into operating commands by work station 206, and are conveyed on bus 232 to control circuit 202. Work station 202 may also supply commands to control the adjustment of the work piece holder 208 and horn 204 to successively locate each channel with respect to the horn surface for each ultrasonic weld cycle. In the weld operating cycle, header module 112 and lid or cover 151 are preferably seated together as shown in FIG. 3 and fitted into work piece holder 208 adjacent ultrasonic horn 204. Contact of the horn surface with the exterior surface of the header module 112 is then established.

Ultrasonic horn 204 is mounted to a pressure fitting 210 controlled by pressure setting circuit 230 to apply a precisely controlled static force of the horn end surface against the outer surface 26 of header module 112 and outer surface 159 of cover or lid 151 positioned at lid recess 147 and disposed on header module surface 26. Emitter or transducer 212 is coupled between pressure fitting 210 and ultrasonic horn 204 and vibrates horn 204 at a predetermined ultrasonic frequency and amplitude and for a predetermined period of time set by time control circuit 218. At the expiration of the predetermined period of time, a cooling time is prescribed before horn 204 is retracted from header module 112 and before the next weld cycle is commenced.

In the ultrasonic welding process, horn 204 is brought into contact with surface 26 and cover 159 at a predetermined static pressure. The applied static pressure is controlled by depth and pressure setting module 230 that responds to a static pressure value command provided by workstation 206 for operating pressure fitting 210 to advance the horn surface against surface 26 and cover 159. An appropriate feedback control signal may be applied to depth and pressure setting module 230. Pressure fitting 210 also controls the penetration depth of the horn 204 into surface 26 of connector module 112 and cover 159 as ultrasonic vibrations are converted into heat energy to melt the thermoplastic material. Control of penetration depth is effected through feedback from linear encoder 232 coupled to horn 204, transducer 212 and pressure fitting 210. The output signal of linear encoder 232 is reset when the static pressure is first applied. The advancement of horn 204 from the initial position is measured and quantified as ultrasonic energy melts the thermoplastic material. When an output signal provided by linear encoder 232 signifies that the desired penetration depth has been is achieved or will be achieved within a certain short period of time, depth and pressure setting module 230 terminates the delivery of pressure to and advancement of horn 204.

During the application and delivery of ultrasonic energy, the amplitude of the ultrasonic vibrations is controlled by amplitude control circuit 216, which responds to input amplitude commands and a processed feedback signal from amplitude detector 214. The amplitude setting signal is applied by an amplitude control circuit to transducer 212, which in turn vibrates horn 204 at a prescribed ultrasonic frequency and amplitude. During the period of time during which ultrasonic welding occurs, the amplitude of the delivered ultrasonic signal is measured and converted to a feedback signal by detector 214. That feedback signal is applied to bridge circuit 220 for comparison to the prescribed amplitude. A difference signal is generated by the bridge circuit 224 that is processed, filtered and amplified by a power circuit 224, filter circuit 226 and amplifier circuit 228 and applied to the amplitude control circuit 216 to modify the amplitude output signal applied to the transducer 212.

Further details and information concerning ultrasonic welding methods, techniques, materials and the like are set forth in the following publications distributed by Branson Ultrasonics Corporation of Danbury, Conn., each such publication hereby being incorporated by reference herein in its respective entirety:

(a) "Designing Parts for Ultrasonic Welding," Technical Information PW-3, ©Branson Ultrasonics Corporation, 1975, printed and revised February, 1996;

(b) "Ultrasonic Stud Welding," Technical Information PW-5, ©Branson Ultrasonics Corporation, 1978, printed April, 1996; and (c) "Textured Surface Technology," TL-4, ©Branson Ultrasonics Corporation, 1975, printed April, 1995. The foregoing publications provide useful information concerning various types of ultrasonic weld joints and techniques such as tongue and groove joints, step joints, textured surfaces, crisscross joints, specialized joints, shear joints, stud welding, staking techniques, standard profile stakes, low profile stakes, dome stakes, knurled stakes, flush stakes, hollow stakes and high pressure stakes, all of which find application in various embodiments of the present invention.

FIGS. 4(a) through 6 show two different embodiments of the present invention, where various header module components are trapped or otherwise secured within header or connector module 112 by ultrasonically welded lid or cover 151. Lid or cover 151 is most preferably formed but not necessarily of the same material as connector or header module 112. Suitable materials for forming connector or header module and lid or cover 151 include medical grade polyurethane, polysulfone and other polymers suitable for implantation within the human body and susceptible to ultrasonic processes.

FIGS. 4(a) through 4(c) show selected views of header module 112 from exploded and assembled top and cross-sectional perspectives, where set screw connector blocks 186 and 188 and grommets 176 and 178 are disposed in corresponding recesses 143, 145 and 147, and secured therewithin by cover 151. Cover or lid 151 is ultrasonically welded to surface 26 of connector module 112 along connector module lip or channel 27 such that initially molten plastic forms and solidifies between cover recess periphery 27 and cover peripheral edge 129 or step 149. Horn 204 (not shown in FIGS. 4(a) through 4(c)) covers and is applied to top or outer surface 159 of cover 151 and the region surrounding lip or channel 27 of connector module 112 during the ultrasonic welding process described hereinabove. Cover 151 and corresponding cover recess 147 are preferably configured such that cover peripheral edge 129 or step 149 matingly engage through tongue and groove joint, step joint or shear joint structural means with corresponding structural means disposed along or in cover recess periphery 27. Other structural means known in the art of ultrasonic welding may also be employed to permit ultrasonic bonding between cover 151 and connector module 112. Medical adhesive may optionally be emplaced between cover 151 and the surface of recess 147 prior to the ultrasonic welding step to provide additional, and highly desirable, increased path length for any bodily fluids that might ingress between cover 151 and connector module 112, and thereby minimize the possibility of an electrical short developing between the set screw connector blocks, for example.

Grommets 176 and 178 are compressed between lower surface 153 of cover 151 and the bottom surface forming cover recess 147 disposed within outer surface 26 of connector module 112. Set screw connector blocks 186 and 188 accept the proximal ends of leads 118 and 116 therewithin, and thereby establish mechanical and electrical connection between the leads and implantable medical device 100. Set screws integral to connector blocks 186 and 188 may be turned and tightened against those distal lead ends by pushing an appropriately configured allen wrench through recesses 155 or 157 and compressible grommets 176 and 178 into set screw recesses 101 and 103. Ultrasonic welding of cover 151 to connector module 112 may eliminate the need to use medical grade adhesive to secure grommets 176 and 178 to connector module 112 and provides other advantages described hereinabove.

FIG. 5 shows another embodiment of the present invention, where multi-beam connectors (MBCs) 191, 193, 195 and 197 are disposed in corresponding recesses 143, 145, 137 and 139 formed in connector module 112, and secured therewithin by cover 151. Cover or lid 151 is ultrasonically welded to surface 26 of connector module 112 along connector module lip or channel 27 such that initially molten plastic forms and solidifies between cover recess periphery 27 and cover peripheral edge 129 or step 149. Horn 204 covers and is applied to top or outer surface 159 of cover 151 and the region surrounding lip or channel 27 of connector module 112 during the ultrasonic welding process described hereinabove.

Cover 151 and corresponding cover recess 147 are preferably configured such that cover peripheral edge 129 or step 149 matingly engage through tongue and groove joint, step joint or shear joint structural means with corresponding structural means disposed along or in cover recess periphery 27. Other structural means known in the art of ultrasonic welding may also be employed to permit ultrasonic bonding between cover 151 and connector module 112. Medical adhesive may optionally be emplaced between cover 151 and recess 147 prior to the ultrasonic welding step to provide additional, and highly desirable, increased path length for any bodily fluids that might ingress between cover 151 and connector module 112, and thereby minimize the possibility of an electrical short developing between feedthrough wire contacts 491, 493, 495 and 497 integral to ribbon connector 131, feedthrough pins 191, 293, 295 and 297, and MBCs 191, 193, 195 and 197, for example.

In those areas where the bottom portions of cover 151 overlap onto and over the feedthrough pin portions of hermetically sealed enclosure 114, cover 151 is generally not ultrasonically welded to enclosure 114. This is because enclosure 114 is usually formed from a biocompatible metal such as titanium, whereas cover 151 is generally formed from a thermoplastic material, and the two dissimilar materials forming cover 151 and enclosure 114 may not be ultrasonically welded to one another. In some embodiments of the present invention, however, cover 151 and enclosure 114 are formed of mutually ultrasonically weldable thermoplastic or polymeric materials.

The embodiment of the present invention shown in FIGS. 5 and 6 eliminates grommets 176 and 178, set screw connector blocks 186 and 188 and a separately supplied allen wrench described in conjunction with FIGS. 4(a) through 4(c) hereinabove. In their stead MBCs 191, 193, 195 and 197, tool 300 and recess 301 are employed as described in further detail in above-referenced U.S. patent application Ser. No. 08/877,033 for "Attachment Apparatus and Method for an Implantable Medical Device Employing Ultrasonic Energy" to Rowley.

Inwardly-facing surface 153 of cover 151 and corresponding outwardly-facing portions of cover recess 147 matingly engage and trap ribbon connector 131 and radio-opaque marker 60 therebetween. Channels, voids and recesses 199 are preferably formed in inwardly facing surface 153 of cover 151 to matingly accept ribbon connector 131 and integral radio-opaque marker 60 therewithin. Ultrasonic welding of cover 151 to connector module 112 may eliminate the need to use medical grade adhesive to secure radio-opaque marker 60, MBCs 191, 193, 195 and 197 and separate feedthrough wires (not shown) to connector module 112, as well as providing other advantages described hereinabove. FIG. 6 shows a side view of medical device 100 of FIG. 5.

Figure 7:
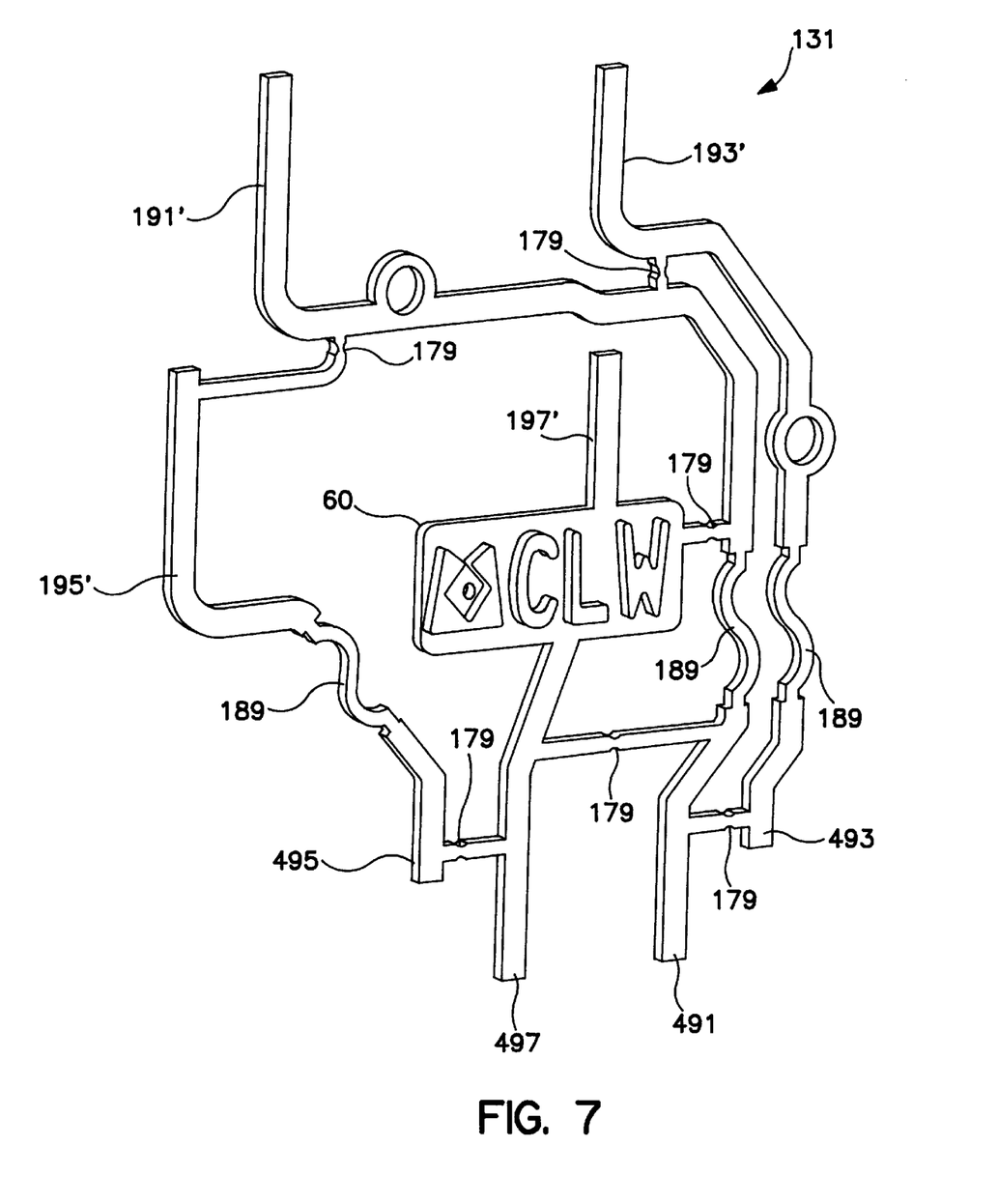
FIG. 7 is a perspective view of the connector ribbon of the present invention.

FIG. 7 shows a perspective view of another embodiment of ribbon connector 131 of the present invention, where strain relief members 189 are shown in greater detail than in FIGS. 5 or 6. Ribbon connector 131 is an interconnect ribbon for connecting feedthrough pins 291, 293, 295 and 297 to MBCs 191, 193, 195 and 197, and owing to its construction provides radio-opaque marker 60 and strain relief members 189 at substantially no additional cost.

Ribbon connector 131 is most preferably formed of 316 L stainless steel, but may also be formed of other corrosion resistant biocompatible metals such as other types of stainless steel, titanium, niobium, tantalum, tungsten, gold, platinum, palladium, alloys or combinations of the foregoing metals, or other suitable metals. It is preferred to form ribbon connector 131 by photo-lithographic means where a resist is placed on a metal sheet having an appropriate structural configuration or shape, the sheet is exposed to light, portions of the sheet masked by the resist are hardened, and portions of the sheet not covered by resist are etched away using an appropriate acid. TECH ETCH, INC.™ of Plymouth, Mass. provides photolithographic etching services suitable for forming ribbon connector 131 of the present invention.

The thickness of the sheet from which ribbon connector 131 is formed most preferably ranges between about 0.004 and about 0.006 inches, although other thickness obviously fall within the scope of the present invention. In contrast, most prior art feedthrough wires have thicknesses of at least about 0.014 inches. Once the photolithographic and etching process has been completed, it is preferred that ribbon connector 131 be bent into its desired final configuration while being emplaced in recess 147, and also while MBCs 191, 193, 195 and 197 and feedthrough pins 291, 293, 295 and 297 are laser or resistance welded to corresponding ribbon connector contacts 191', 193', 195', 197' and 491, 493, 495 and 497. Emplacement, bending and welding of connector ribbon 131 occur before cover 151 is emplaced in recess 147 and ultrasonically welded to connector module 112. Additionally, bridges 179 disposed between adjoining contacts and ribbons of ribbon connector 131 are severed prior to attachment of cover 151 to connector module 112 and after connector ribbon 131 has been welded to corresponding MBCs and feedthrough pins. Such severing is most preferably accomplished using means.

Ribbon connector 131 of the present invention provides the advantages of: (a) eliminating the step of hand forming feedthrough wires; (b) permitting or facilitates automation of final assembly of implantable medical devices; (c) providing strain relief for feedthrough connections at substantially no extra cost; (d) providing radio-opaque markers at substantially no extra cost; (d) permitting the design and manufacture of reduced thickness or profile implantable medical devices.

The above described methods and apparatus for attaching covers or lids to a connector or header module for an implantable medical device may be applied to a wide variety of implantable medical devices having a variety of header or connector module or hermetically sealed enclosure configurations. The principle of the present invention may be extended to various permutations and combinations of such components in many different types of implantable medical devices.

The preceding specific embodiments are illustrative of the practice of the invention. It is understood therefore that other expedients and equivalents of disclosed components or functions known to those of skill in the art or otherwise disclosed herein may be employed in practicing the invention without departing from the invention or the scope of the following claims.

In the following claims, means-plus-function clauses are intended to cover the structures described herein as performing the recited function and not only structural equivalents but also equivalent structures. For example, although a nail and a screw may not be structural equivalents in that a nail employs a cylindrical surface to secure wooden parts together, whereas a screw employs a helical surface, in the environment of fastening wooden parts, a nail and a screw are equivalent structures.

We claim:

1. A method of securing at least one component within a pre-formed module including a pre-formed header module and a connector module attached to a hermetically sealed enclosure of an implantable medical device, wherein said hermetically sealed enclosure is formed with a plurality of electrical feedthrough, each feedthrough having a feedthrough pin extending through an enclosure wall for attachment with a like plurality of connector components located within a like plurality of component recesses, including making an electrical connection which comprises the steps of:

forming a ribbon connector of a plurality of conductive ribbons and a radiopaque marker joined by bridges, each ribbon having first and second ribbon connector contacts;

attaching each of said first ribbon connector contacts to a terminal of a feedthrough pin;

attaching each of said second ribbon connector contact to one of said connector components; and     severing said bridges to electrically isolate each of said ribbons and said radiopaque marker.

2. The method of claim 1, further including a step of forming a recess cover by shaping an inward facing recess cover to accommodate all of said ribbons and said radiopaque marker separated from contact with one another.

3. The method of claim 2, wherein said connector components comprise multi-beam connectors.

4. The method of claim 1, wherein said connector component comprises a multi-beam connector.

5. The method of claim 1, wherein the preformed module is formed of a thermoplastic material having an outer surface comprising an attachment surface and an exposed module surface and is configured for attachment at said attachment surface to a mating surface of the hermetically sealed enclosure.

6. The method of claim 5 wherein each component recess in the enclosure is formed in the exposed module surface and bounded by a recess outer periphery.

7. The method of claim 6 further including a step of forming a recess cover of thermoplastic material having a cover surface comprising an outward facing surface bounded by a cover peripheral edge and an inward facing surface, said cover peripheral edge being shaped to match the recess outer periphery of the component recess and to position the inward facing surface in overlying relation to the recess outer periphery and to form a first mating surface in overlying relation to the recess outer periphery and to form a first mating surface for mating with a second mating surface formed on the exposed module surface adjacent the recess outer periphery.

8. The method of claim 6 further including a step of isolating a component within a component recess and sealing the recess cover against ingress of body fluids by applying ultrasonic welding energy against the recess cover and the exposed module surface in a region of the first and second mating surfaces thereof for a time period sufficient to effect a melting of the thermoplastic materials and ultrasonic welding of the recess cover to the preformed module upon removal of the ultrasonic energy.

\* \* \* \* \*

UNITED STATES PATENT AND TRADEMARK OFFICE
CERTIFICATE OF CORRECTION

PATENT NO. : 6,205,358 B1
DATED : March 20, 2001
INVENTOR(S) : Haeg et al.

It is certified that error appears in the above-identified patent and that said Letters Patent is hereby corrected as shown below:

<u>Title page,</u>
Item [54], Title "METHOD OF MAKING ULTRASONICALLY WELDED, STAKED OF SWAGED..." should read -- METHOD OF MAKING ULTRASONICALLY WELDED, STAKED OR SWAGED --

Signed and Sealed this

Ninth Day of April, 2002

Attest:

*Attesting Officer*

JAMES E. ROGAN
*Director of the United States Patent and Trademark Office*